United States Patent [19]

Sanderson et al.

[11] Patent Number: 4,922,036

[45] Date of Patent: * May 1, 1990

[54] TERTIARY BUTYL HYDROPEROXIDE DECOMPOSITION

[75] Inventors: John R. Sanderson, Leander; Edward T. Marquis; John F. Knifton, both of Austin, all of Tex.

[73] Assignee: Texaco Inc., White Plains, N.Y.

[*] Notice: The portion of the term of this patent subsequent to Mar. 27, 2007 has been disclaimed.

[21] Appl. No.: 94,175

[22] Filed: Sep. 8, 1987

[51] Int. Cl.$^5$ .................. C07C 31/12; C07C 29/132; C07C 29/88; C07C 27/04
[52] U.S. Cl. .................. 568/909.8; 502/163; 568/910; 568/914; 568/922; 568/571
[58] Field of Search .................. 568/571, 840 A, 910, 568/914, 922, 909.8; 502/163

[56] References Cited

U.S. PATENT DOCUMENTS

| | | | |
|---|---|---|---|
| 3,360,585 | 12/1967 | Winnick | 568/840 |
| 3,505,360 | 4/1970 | Allison et al. | 568/840 |
| 4,508,923 | 4/1985 | Taylor et al. | 568/840 |
| 4,547,598 | 10/1985 | Sanderson et al. | 568/840 |
| 4,551,553 | 11/1985 | Taylor et al. | 568/840 |

FOREIGN PATENT DOCUMENTS

1212824 11/1970 United Kingdom ............ 568/909.8

*Primary Examiner*—Vivian Garner
*Attorney, Agent, or Firm*—Jack H. Park; Kenneth R. Priem; Carl G. Ries

[57] ABSTRACT

Tertiary butyl alcohol is prepared by the catalytic decomposition of tertiary butyl hydroperoxide, preferably in solution in tertiary butyl alcohol, in the presence of a borate-promoted metal phthalocyanine catalyst such as a Group IB, VIIB or VIIIB metal phthalocyanine and a Group IA, IIA or IIB metal borate, for example, chloroferric phthalocyanine and lithium borate, barium borate, zinc borate or sodium metaborate.

15 Claims, No Drawings

TERTIARY BUTYL HYDROPEROXIDE DECOMPOSITION

BACKGROUND OF THE INVENTION

1. Field of the Invention

This invention relates to the catalytic decomposition of tertiary butyl hydroperoxide. More particularly, this invention relates to a method for the preparation of tertiary butyl alcohol by the catalytic decomposition of tertiary butyl hydroperoxide. Still more particularly, this invention relates to a method wherein a borate-promoted phthalocyanine is used to catalyze the substantially selective decomposition of tertiary butyl hydroperoxide to tertiary butyl alcohol.

2. Prior Art

It is known to react isobutane with oxygen, either thermally or catalytically, to form a peroxidation reaction product wherein the principal peroxide that is formed is tertiary butyl hydroperoxide. It is also known to thermally or catalytically decompose the tertiary butyl hydroperoxide to form tertiary butyl alcohol.

The metal phthalocyanines are known compounds, described for example in the ACS Monograph Series by F. H. Moser and A. L. Thomas entitled "Phthalocyanine Compounds" (Rhinehold Publishing Corp.).

Williams et al. U.S. Pat. No. 3,816,548 is directed to a liquid phase oxidation process for oxidizing an isoparaffin hydrocarbon such as isobutane to an alcohol such as tertiary butyl alcohol in the presence of certain metal phthalocyanine catalysts.

Klein in U.S. Pat. No. 3,472,876, discloses the use of cobalt diimine chelates to catalyze the reaction of oxygen with an olefin to form an olefin epoxide.

Quin U.S. Pat. No. 2,854,487 discloses a process wherein isopropyl benzene hydroperoxides are catalytically decomposed to form carbinole in the presence of hydrogen and a catalyst composed of palladium supported on activated alumina.

Grane U.S. Pat. No. 3,474,151 discloses that tertiary butyl alcohol starts to dehydrate at 450° C. and to decompose at a "rapid rate" at temperatures above 475° F. Grane discovered, however, that residual quantities of hydroperoxide contaminants present in tertiary butyl alcohol could be thermally decomposed by heating the contaminated tertiary butyl alcohol at a temperature of 375° to 475° F. for about 1 to 10 minutes. Heating tertiary butyl alcohol containing small amounts of peroxides at high temperatures for even short periods of time to remove the peroxides produces undesirable products such as isobutylene.

Grane et al. U.S. Pat. No. 4,294,999 discloses a process wherein isobutane is oxidized in a pressured reactor in the presence of a solubilized molybdenum catalyst to provide a mixture of tertiary butyl alcohol, tertiary butyl hydroperoxide, methanol, acetone, and other oxygen-containing compounds. The tertiary butyl hydroperoxide is thermally decomposed under pressure at about 280° F. to provide a tertiary butyl alcohol product containing only residual quantities of tertiary butyl hydroperoxide which are then decomposed in accordance with Grane U.S. Pat. No. 3,474,151 by heating the tertiary butyl alcohol at 375° to 475° for about 1 to 10 minutes.

Grane et al. U.S. Pat. No. 4,296,262 discloses a related process wherein isobutane is reacted with oxygen in a reaction zone for a residence time of about 1 to 10 hours at a temperature of about 240° to about 340° F. and a pressure of about 100 to about 1000 psig. in the presence of a catalytically effective amount of a soluble molybdenum catalyst. A liquid stream comprising tertiary butyl alcohol is recovered from the reaction mixture and fed to a decomposition zone wherein the tertiary butyl hydroperoxide contained therein is decomposed by "hot aging" at 250°–850° F. at a pressure lower than the pressure in the oxidation zone. The tertiary butyl alcohol can be further subjected to a cleanup treatment at 375°–475° F. for 1 to 10 minutes. Worrell et al. in U.S. Pat. No. 4,296,263 disclose a related process wherein the feedstock is a mixture of normal butane with isobutane and wherein the oxidation catalyst is a soluble form of chromium, cobalt, nickel, manganese, molybdenum, or a mixture thereof.

When isobutane is reacted with molecular oxygen, the principal products of the reaction are tertiary butyl alcohol and tertiary butyl hydroperoxide. However, minor amounts of other peroxides, including ditertiary butyl peroxide are also formed. Generally speaking, from about 10 to about 100 parts of tertiary butyl hydroperoxide are formed per part of ditertiary butyl peroxide. Minor quantities of other contaminants are also formed.

In addition, a minor amount of water will be formed, which will normally amount to about 0.5 to 1 wt.% of the reactor effluent. The amount of byproduct water that is produced is a function of the severity of the reaction conditions employed and will tend to increase as the severity of the reaction conditions is increased.

A listing of the components present in a representative reaction product from the reaction of isobutane and oxygen and their nominal boiling points is given in Table A.

TABLE A

| Component | NBP (°C.) |
| --- | --- |
| Isobutane | −11.7 |
| Methyl formate | 31.8 |
| Acetone | 56.3 |
| Isobutylene oxide | 60.0 |
| Isobutyraldehyde | 64.1 |
| Methanol | 64.7 |
| Methyl-t-butyl peroxide | 74.2 |
| Isopropyl alcohol | 82.3 |
| Tertiary butyl alcohol | 82.4 |
| Ditertiary butyl peroxide | 111.0 |
| Tertiary butyl hydroperoxide | 118.9 |
| t-butyl-i-pr-peroxide | 124.0 |
| Tertiary butyl formate | 163.8 |

The minor by-products are sometimes difficult to remove. For example, tertiary butyl formate has a higher boiling point than ditertiary butyl peroxide but tends to distill overhead, which suggests that it forms a minimum boiling azeotrope with another component or components.

As indicated, tertiary butyl hydroperoxide is useful as a raw material for the manufacture of tertiary butyl alcohol. The tertiary butyl alcohol can be formed by catalytic decomposition of the tertiary butyl hydroperoxide. In the Williams et al. process disclosed in U.S. Pat. No. 3,472,876, an oxygen-containing gas was charged to a reactor containing isobutane and an oxidation catalyst to provide a reaction mixture comprising tertiary butyl alcohol, tertiary butyl hydroperoxide, acetone, and tertiary butyl ether. The reported results in the patent indicate that there was a comparatively low rate of conversion and a comparatively poor selectivity of the reaction to tertiary butyl alcohol.

SUMMARY OF THE INVENTION

In accordance with the present invention, isobutane is reacted with oxygen in an oxidation zone to provide an oxidation product comprising a solution of tertiary butyl hydroperoxide in tertiary butyl alcohol and unreacted isobutane. A catalyst may be present to catalyze the reaction of the oxygen with the isobutane if desired.

A suitable feedstock is used, such as one prepared by the oxidation of isobutane with molecular oxygen to provide an oxidation reaction product containing a solution of tertiary butyl hydroperoxide in tertiary butyl alcohol and unreacted isobutane. The feedstock may comprise tertiary butyl hydroperoxide dissolved in tertiary butyl alcohol which is recovered from the oxidation reaction product. The feedstock is charged to a catalytic decomposition zone wherein the tertiary butyl hydroperoxide is decomposed in the presence of a borate-promoted chloroferric phthalocyanine catalyst to provide a decomposition reaction product characterized by a comparatively high conversion rate and a comparatively high selectivity of tertiary butyl hydroperoxide to tertiary butyl alcohol.

The tertiary butyl alcohol will not be the only decomposition product that is formed. A minor amount of ditertiary butyl peroxide will also be formed together with other oxygen-containing materials such as those listed above.

The tertiary butyl alcohol that is recovered from the decomposition reaction mixture will be contaminated with ditertiary butyl peroxide and other oxygenated impurities.

The ditertiary butyl peroxide can be recovered, if desired, by a process such as the process disclosed in copending Sanderson et al. U.S. patent application Ser. No. 06/945,628, filed Dec. 23, 1986, and entitled "Recovery of Purified Ditertiary Butyl Peroxide" or the process disclosed in copending application Ser. No. 06/945,629, filed Dec. 23, 1986 by Sanderson et al., and entitled "Ditertiary Butyl Peroxide Recovery", now U.S. Pat. No. 4,810,809.

If desired, the ditertiary butyl peroxide and other contaminants may be removed from the tertiary butyl alcohol product by a catalytic purification process such as, for example, the purification process disclosed in copending Sanderson et al. U.S. patent application Ser. No. 06/836,798, filed Mar. 6, 1986, now abandoned, and entitled "Removal of Peroxide Contaminants from Tertiary Butyl Alcohol Using a Nickel Catalyst", or by a purification process disclosed in copending Sanderson et al. U.S. patent application Ser. No. 06/926,159, filed Nov. 3, 1986, and entitled "Catalytic Removal of Peroxide Contaminants from Tertiary Butyl Alcohol," now U.S. Pat. No. 4,742,179, issued May 3, 1988, or by the process disclosed in copending Sanderson et al. application Ser. No. 06/932,822, filed Nov. 20, 1986, and entitled "Catalytic Decomposition of Impurities in Tertiary Butyl Alcohol," now U.S. Pat. No. 4,705,903, issued Nov. 10, 1987, or, as yet another example, by the process disclosed in copending Sanderson et al. U.S. patent application Ser. No. 07/004,508, filed Jan. 30, 1987, now Pat. No. 4,873,380, and entitled "Catalyst for Removing Peroxide Contaminants from Tertiary Butyl Alcohol".

DESCRIPTION OF THE PROCESS OF THE PRESENT INVENTION

The starting materials for the process of the present invention are tertiary butyl hydroperoxide, a metal phthalocyanine catalyst, a metal borate promoter and a solvent.

The metal phthalocyanine catalyst used in this invention is suitably a phthalocyanine of a heavy metal selected from the Group IB, Group VIIB, or Group VIIIB of the Periodic Table.

Phthalocyanine itself is:

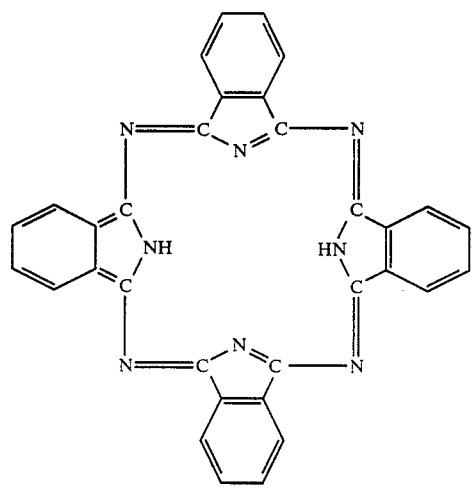

The two hydrogens in the center of the molecule are replaced by metals from these groups. The metals may be in a high oxidation state or a lower oxidation state. For example, Ferric ($Fe^{+++}$) or Ferrous ($Fe^{++}$) may be used. In addition, from 1 to 16 of the peripheral hydrogen atoms on the 4 benzene rings may be replaced with halogen atoms and by numerous organic and inorganic groups. Suitable phthalocyanines include cobalt phthalocyanine, copper phthalocyanine, chloroferric phthalocyanine, ferrous phthalocyanine, manganese phthalocyanine, and ruthenium phthalocyanine.

Any appropriate metal borate promoter may be used, such as an alkali metal borate, an alkaline earth metal borate, a borate of a Group IA, Group IIA or Group IIB metal, etc. Examples of appropriate metal borates include compounds such as sodium borate, lithium borate, magnesium borate, zinc borate, calcium borate, barium borate, sodium metaborate, lithium metaborate, ammonium borate, etc. Mixtures of two or more such metal borates may be used, if desired.

The solvent to be used in practicing the process of the present invention may be any suitable organic solvent in which tertiary butyl hydroperoxide is soluble at least to an extent sufficient to provide a solution containing from about 2 to about 90 wt.% of tertiary butyl hydroperoxide. A preferred solvent is isobutane and a still more preferred solvent is tertiary butyl alcohol. In accordance with the most preferred embodiment of the present invention, the charge material for the process will comprise about a 20 to about a 50 wt.% or about a 5 to about a 30 wt.% solution of tertiary butyl hydroperoxide and tertiary butyl alcohol.

The process of the present invention may be conducted batchwise in kettles or by continuously passing the reactants through a reactor.

In any event, the solvent solution of tertiary butyl hydroperoxide that is charged to the reaction zone will also have dissolved or slurried therein from about 0.001 to about 5 wt.%, based on the weight of the tertiary butyl hydroperoxide, of a metal phthalocyanine catalyst and from about 1 to about 6 parts by weight of metal borate promoter, per part of chloroferric phthalocyanine catalyst.

The catalytic decomposition of the tertiary butyl hydroperoxide is conducted at a temperature of about 20% to about 125° C., preferably conducted at a temperature within the range of about 20° to about 80° C. and, more preferably, at a temperature within the range of about 20° to about 60° C. The reaction is preferably conducted at autogenous pressure although superatmospheric pressures up to about 1000 psig. may be used, if desired.

Flow rates of the charge solution to the reaction zone should be adjusted in order to provide an appropriate contact time within the reactor. In a batch process, the holding time may suitably be from about 0.5 to about 10 hours.

In accordance with the most preferred embodiment of the present invention, isobutane is reacted with oxygen in an oxidation zone under oxidation reaction conditions including a temperature of about 135° to about 155° C., a pressure of about 300 to about 800 psig., and a holding time of about 0.5 to about 5 hours to provide an initial oxidation reaction product comprising unreacted isobutane, tertiary butyl hydroperoxide, and some tertiary butyl alcohol. The oxidation reaction product is fractionated in any appropriate manner (e.g., by distillation in a distillation zone) to remove the isobutane therefrom for recycle and to provide a solution of tertiary butyl hydroperoxide and tertiary butyl alcohol which will normally contain from about 5 to about 30 wt.% of tertiary butyl hydroperoxide. If the tertiary butyl hydroperoxide concentration is excessive, additional tertiary butyl alcohol may be added.

The solvent solution of tertiary butyl hydroperoxide in organic solvents (e.g., tertiary butyl alcohol solvent solution of tertiary butyl hydroperoxide) is then charged to a catalytic hydroperoxide decomposition zone where it is brought into contact with a borate-promoted metal phthalocyanine catalyst to substantially selectively convert the tertiary butyl hydroperoxide to tertiary butyl alcohol with high yields and selectivities.

The reaction product from the tertiary butyl hydroperoxide decomposition step may then be fractionated in any suitable manner, such as, for example, in the manner shown in the process disclosed in above identified copending U.S. patent application Ser. No. 06/945,628 filed Dec. 23, 1986. In accordance with a process recovery sequence of this nature, both the tertiary butyl alcohol and the ditertiary butyl peroxide will be recovered in purified form as products of the reaction.

Alternately, a crude tertiary butyl alcohol product stream contaminated with ditertiary butyl peroxide and other contaminants may be obtained which will then be further treated either thermally, in accordance with the process of the Grane et al. U.S. patents, or catalytically by one of the processes disclosed in the copending Sanderson et al. patent applications to convert the ditertiary butyl peroxide to tertiary butyl alcohol and to otherwise significantly reduce the level of contamination of the other oxygen-containing impurities.

SPECIFIC EXAMPLES

The invention will be further illustrated by the following specific examples which are given by way of illustration and not as limitations on the scope of this invention.

Procedure: Tube Experiments

A 150-ml Fisher-Porter pressure tube equipped with pressure gauge, rupture disk, and shut-off valve was charged with 15.0 g of an 18.43% TBHP solution in TBA, and catalyst(s). The tube was suspended in a constant temperature bath (+ or −0.2° C.) for the desired period of time at the required temperature. The tube was shaken from time to time during the run. At the end of the run, the tube was placed in cold water (15°–20° C.) for 15 minutes. The pressure was then slowly released. The contents were analyzed by GC. The results are shown in the attached Table I.

TABLE I

Decomposition of tert-Butyl Hydroperoxide in the Presence of Iron Phthalocyanine and an Alkali Metal Borate[a]

| N.B. Number | Catalyst(s)[b] | Time (Hr) | Temp (°C.) | TBHP | TBA | Acetone | MeOH | DTBP |
|---|---|---|---|---|---|---|---|---|
| 6274-10 | Fe(III)PCYCl[.01 g] | 1.0 | 40.0 | 3.65 | 93.59 | 0.31 | <0.1 | 2.12 |
| 6274-23 | Fe(III)PCYCl[.01 g] LiBO$_2$[.02 g] | 1.0 | 40.0 | 0.13 | 96.31 | 0.73 | <0.1 | 2.14 |
| 6274-26 | Fe(III)PCYCl[.01 g] LiBO$_2$[.01 g] | 1.0 | 40.0 | 0.52 | 96.03 | 0.64 | <0.1 | 2.15 |
| 6274-41 | Fe(III)PCYCl[.01 g] LiBO$_2$[.05 g] | 1.0 | 40.0 | 0.17 | 96.32 | 0.57 | <0.1 | 2.20 |
| 6274-27 | Fe(III)PCYCl[.01 g] Ba(BO$_2$)$_2$[.01 g] | 1.0 | 40.0 | 0.89 | 95.65 | 0.77 | <0.1 | 2.23 |
| 6274-28 | Fe(III)PCYCl[.01 g] Zn(BO$_2$)$_2$[.01 g] | 1.0 | 40.0 | 0.54 | 96.10 | 0.65 | <0.1 | 2.22 |
| 6274-22 | Fe(III)PCYCl[.01 g] Na$_2$B$_2$O$_4$.8H$_2$O[.02 g] | 1.0 | 40.0 | 0.53 | 96.17 | 0.63 | <0.1 | 2.24 |
| 6274-24 | Fe(III)PCYCl[.01 g] Na$_2$B$_2$O$_4$.8H$_2$O[.02 g] | 1.0 | 40.0 | 0.51 | 96.15 | 0.66 | <0.1 | 2.23 |
| 6274-39 | Fe(III)PCYCl[.01 g] Na$_2$B$_2$O$_4$.8H$_2$O[.05 g] | 1.0 | 40.0 | 0.52 | 96.00 | 0.78 | <0.1 | 2.25 |
| 6274-31 | LiBO$_2$[.02 g] | 1.0 | 40.0 | No Reaction | | | | |

TABLE I-continued

Decomposition of tert-Butyl Hydroperoxide in the Presence of Iron Phthalocyanine and an Alkali Metal Borate[a]

| N.B. Number | Catalyst(s)[b] | Time (Hr) | Temp (°C.) | TBHP | TBA | Acetone | MeOH | DTBP |
|---|---|---|---|---|---|---|---|---|
| — | Starting Material | | | 18.43 | 81.02 | 0 | 0 | 0.06 |

Products Wt. %[c,d]

[a]The initial TBHP concentration was 18.34% - remainder mostly TBA. 15.6 g changed.
[b]PCY = Phthalocyanine
[c]Determined by GC (Hewlett-Packart 5890, 3392A Integrator)
[d]Fused silica capillary column, 5% methyl phenyl silicone oil, 0.53 mm ID, 3.0μ film program, 35-165° C.

Discussion of Data in Table

Chloroferric phthalocyanine alone catalyzes the decomposition of TBHP to TBA. In one hour at 40° C., 3.65% of the TBHP in a 15.0 g initial charge remains when using 0.01 g of the phthalocyanine (6274-10). Under the same conditions but with the addition of lithium borate, 0.13 to 0.17% tertiary butyl hydroperoxide remains without loss of selectivity to tertiary butyl alcohol (runs 6274-23, 6274-26 and 6274-41). Other metal borates such as barium borate, sodium borate, and zinc borate are also effective. Control experiments show that lithium borate alone does not catalyze the decomposition of TBHP under the reaction conditions (6274-31).

Having thus described our invention, what is claimed is:

1. In a method wherein a t-butyl hydroperoxide charge stock is brought into contact with a catalytically effective amount of a hydroperoxide decomposition catalyst in a hydroperoxide decomposition reaction zone in liquid phase with agitation to convert said t-butyl hydroperoxide to decomposition products, principally t-butyl alcohol, the improvement which comprises:
   (a) using, as said hydroperoxide decomposition catalyst, a borate-promoted metal phthalocyanine catalyst,
   (b) recovering said t-butyl alcohol from the products of said hydroperoxide decomposition reaction, and
   (c) said metal of said metal phthalocyanine catalyst being a heavy metal selected from the group consisting of heavy metals of Groups IB, VIIB or VIIIB of the Periodic Table,
   (d) said borate of said borate-promoted metal phthalocyanine catalyst being a borate selected from the group consisting of ammonium borate and metal borates of metals of Group IA alkali metal, Group IIA alkaline earth metal and Group IIB of the Periodic Table.

2. In a method wherein a solution of a t-butyl hydroperoxide charge stock in t-butyl alcohol is brought into contact with a catalytically effective amount of a hydroperoxide decomposition catalyst in a hydroperoxide decomposition reaction zone in liquid phase with agitation under hydroperoxide decomposition reaction conditions to convert said t-butyl hydroperoxide to decomposition products, principally t-butyl alcohol, the improvement which comprises:
   (a) charging a t-butyl alcohol solution of a borate and a metal phthalocyanine catalyst to said hydroperoxide decomposition reaction zone as said hydroperoxide decomposition catalyst,
   (b) removing said t-butyl alcohol from the products of said hydroperoxide decomposition reaction, and
   (c) said metal of said metal phthalocyanine catalyst being a heavy metal selected from the group consisting of heavy metals of Groups IB, VIIB or VIIIB of the Periodic Table,
   (d) said borate of said borate-promoted metal phthalocyanine catalyst being a borate selected from the group consisting of ammonium borate and metal borates of metals of Group IA alkali metal, Group IIA alkaline earth metal and Group IIB of the Periodic Table.

3. In a method wherein a charge stock comprising a solution of t-butyl hydroperoxide in t-butyl alcohol is brought into contact with a catalytically effective amount of a hydroperoxide decomposition catalyst in a hydroperoxide decomposition reaction zone in liquid phase with agitation under hydroperoxide decomposition reaction conditions to convert said t-butyl hydroperoxide to decomposition products, principally t-butyl alcohol, the improvement which comprises:
   (a) preparing a t-butyl alcohol solution of a metal phthalocyanine catalyst and a borate,
   (b) charging said t-butyl alcohol solution of said borate and said metal phthalocyanine catalyst to said hydroperoxide decomposition reaction zone as said hydroperoxide decomposition catalyst,
   (c) recovering said t-butyl alcohol from the products of said hydroperoxide decomposition reaction, and
   (d) said metal of said metal phthalocyanine catalyst being a heavy metal selected from the group consisting of heavy metals of Groups IB, VIIB or VIIIB of the Periodic Table,
   (e) said borate of said borate-promoted metal phthalocyanine catalyst being a borate selected from the group consisting of ammonium borate and metal borates of metals of Group IA alkali metal, Group IIA alkaline earth metal and Group IIB of the Periodic Table.

4. A method as in claim 3 wherein the metal phthalocyanine catalyst is chloroferric phthalocyanine.

5. A method as in claim 4 wherein the borate is an alkali metal borate.

6. A method as in claim 5 wherein the alkali metal borate is lithium borate.

7. A method as in claim 5 wherein the alkali metal borate is sodium borate.

8. A method as in claim 4 wherein the borate is an alkaline earth metal borate.

9. A method as in claim 8 wherein the alkaline earth metal borate is magnesium borate.

10. A method as in claim 8 wherein the alkaline earth metal borate is calcium borate.

11. A method as in claim 8 wherein the alkaline earth metal borate is barium borate.

12. A method as in claim 4 wherein the borate is a Group IIB metal borate.

13. A method as in claim 12 wherein the Group IIB metal borate is zinc borate.

14. In a continuous method for preparing t-butyl alcohol wherein isobutane is continuously reacted with molecular oxygen in an oxidation reaction zone under liquid phase oxidation reaction conditions to provide an initial reaction mixture comprising unreacted isobutane and isobutane oxidation reaction products, principally t-butyl hydroperoxide and t-butyl alcohol, wherein unreacted isobutane is continuously separated from said initial reaction mixture to provide a charge stock comprising a solution of said t-butyl hydroperoxide in said t-butyl alcohol, containing from about 2 to about 90 wt.% of t-butyl hydroperoxide, wherein said charge stock is continuously charged to a hydroperoxide decomposition zone, and wherein a catalytic hydroperoxide decomposition reaction is continuously conducted in said decomposition reaction zone to convert said t-butyl hydroperoxide to decomposition products, principally t-butyl alcohol, to provide a hydroperoxide conversion product, the improvement which comprises:

(a) adding to said charge stock as said hydroperoxide decomposition catalyst from about 0.001 to about 5 wt.%, based on the weight of the t-butyl hydroperoxide of chloroferric phthalocyanine and about 1 to 6 parts by weight, per part of the chloroferric phthalocyanine of a borate selected from the group consisting of ammonium borate and metal borates of metals of Group IA alkali metal, Group IIA alkaline earth metal or Group IIB of the Periodic Table, (b) conducting said hydroperoxide decomposition reaction in the presence of said hydroperoxide decomposition catalyst in said hydroperoxide decomposition zone in liquid phase with agitation under reaction conditions including a temperature within the range of about 20° to about 125° C. and autogenous pressure, (c) continuously removing a stream of said hydroperoxide conversion product from said hydroperoxide conversion zone, and (d) continuously recovering t-butyl alcohol from said stream of said hydroperoxide conversion product.

15. In a continuous method for preparing t-butyl alcohol wherein isobutane is continuously reacted with molecular oxygen in an oxidation reaction zone under liquid phase oxidation reaction conditions to provide an initial reaction mixture comprising unreacted isobutane and isobutane oxidation reaction products, principally t-butyl hydroperoxide and t-butyl alcohol, wherein unreacted isobutane is continuously separated from said initial reaction mixture to provide a charge stock comprising a solution of said t-butyl hydroperoxide in said t-butyl alcohol, containing from about 20 to about 50 wt.% of t-butyl hydroperoxide, wherein said charge stock is continuously charged to a hydroperoxide decomposition zone, and wherein a catalytic hydroperoxide decomposition reaction is continuously conducted in said decomposition reaction zone to convert said t-butyl hydroperoxide to decomposition products, principally t-butyl alcohol, to provide a hydroperoxide conversion product, the improvement which comprises:

(a) adding to said charge stock as said hydroperoxide decomposition catalyst from about 0.001 to about 5 wt.%, based on the weight of the t-butyl hydroperoxide of chloroferric phthalocyanine and about 1 to 6 parts by weight, per part of the chloroferric phthalocyanine of a lithium, sodium, magnesium, zinc, or calcium borate, (b) conducting said hydroperoxide decomposition reaction in the presence of said hydroperoxide decomposition catalyst in said hydroperoxide decomposition zone in liquid phase with agitation under reaction conditions including a temperature within the range of about 20° to about 125° C. and autogenous pressure, (c) continuously removing a stream of said hydroperoxide conversion product from said hydroperoxide conversion zone, and (d) continuously recovering t-butyl alcohol from said stream of said hydroperoxide conversion product.

* * * * *